US012636255B2

(12) United States Patent
Arumugam et al.

(10) Patent No.: US 12,636,255 B2
(45) Date of Patent: May 26, 2026

(54) NONGRANULATED COMPRESSED TABLETS OF MESALAMINE, AND PROCESS OF PREPARATION THEREOF

(71) Applicant: ATOZ PHARMACEUTICALS PVT LTD, Chennai (IN)

(72) Inventors: Olaganathan Arumugam, Chennai (IN); Natarajan Venkatachalam, Chennai (IN)

(73) Assignee: ATOZ PHARMACEUTICALS PVT LTD, Chennai (IN)

( * ) Notice: Subject to any disclaimer, the term of this patent is extended or adjusted under 35 U.S.C. 154(b) by 0 days.

(21) Appl. No.: 17/508,238

(22) Filed: Oct. 22, 2021

(65) Prior Publication Data

US 2022/0125733 A1     Apr. 28, 2022

(30) Foreign Application Priority Data

Oct. 23, 2020    (IN) ............................ 202041046393

(51) Int. Cl.
*A61K 9/48* (2006.01)
*A61K 31/196* (2006.01)

(52) U.S. Cl.
CPC .......... *A61K 9/4808* (2013.01); *A61K 9/4825* (2013.01); *A61K 9/4833* (2013.01); *A61K 9/485* (2013.01); *A61K 9/4891* (2013.01); *A61K 31/196* (2013.01)

(58) Field of Classification Search
CPC .. A61K 9/4808; A61K 9/4825; A61K 9/4833; A61K 9/485; A61K 9/4891; A61K 31/196
See application file for complete search history.

(56) References Cited

U.S. PATENT DOCUMENTS

| | | | | |
|---|---|---|---|---|
| 3,396,226 A | * | 8/1968 | Cavalli ................ | A61K 9/2004 |
| | | | | 514/474 |
| 10,688,057 B2 | * | 6/2020 | Boyd ................... | A61K 9/4808 |
| 2003/0185885 A1 | * | 10/2003 | Franz ................... | A61K 31/195 |
| | | | | 514/567 |
| 2007/0020335 A1 | * | 1/2007 | Chen .................... | A61K 9/2866 |
| | | | | 424/486 |
| 2009/0028944 A1 | * | 1/2009 | Sathurappan ........ | A61K 9/2027 |
| | | | | 514/567 |
| 2013/0195980 A1 | * | 8/2013 | Jepsen ..................... | A61P 1/00 |
| | | | | 424/490 |
| 2015/0056275 A1 | * | 2/2015 | Bowe ...................... | A61P 29/00 |
| | | | | 424/480 |
| 2015/0196518 A1 | * | 7/2015 | Khera .................. | A61K 31/196 |
| | | | | 53/436 |
| 2019/0060277 A1 | * | 2/2019 | Laudon ................ | A61K 9/2072 |
| 2019/0105275 A1 | * | 4/2019 | Liang ................... | A61K 9/2846 |
| 2022/0047515 A1 | * | 2/2022 | Pedrani ................ | A61K 9/2846 |

OTHER PUBLICATIONS

A Guidebook to Particle Size Analysis. By Horiba Scientific. 2017, 34 pages. (Year: 2017).*
Thoorens et al. Microcrystalline cellulose, a direct compression binder in a quality by design environment—A review. International Journal of Pharmaceutics 473 (2014) 64-72. (Year: 2014).*
Thoorens et al. Understanding the impact of microcrystalline cellulose physicochemical properties on tabletability. International Journal of Pharmaceutics 490 (2015) 47-54. (Year: 2015).*

* cited by examiner

*Primary Examiner* — Robert A Wax
*Assistant Examiner* — Olga V. Tcherkasskaya

(57) ABSTRACT

The present disclosure discloses a composition suitable for direct compression into tablets without prior granulation procedures comprising: a) mesalamine or its prodrug or derivatives thereof and b) at least one pharmaceutically acceptable excipient, wherein the composition is directly compressed into a minitablet such that largest dimension in the minitablet is range of 1.00 mm to 2.8 mm. Further disclosed is a process of preparation of composition of the present disclosure.

5 Claims, No Drawings

NONGRANULATED COMPRESSED TABLETS OF MESALAMINE, AND PROCESS OF PREPARATION THEREOF

FIELD OF THE INVENTION

The present disclosure broadly relates to the field of pharmaceutical compositions, and particularly relates to compositions for preparing non granulated solid oral dosage forms of mesalamine or its prodrugs or derivatives thereof and process of preparing the same. The present application is based on, and claims priority from an Indian Application No. 202041046393 filed on 23 Oct. 2020, the disclosure of which is hereby incorporated by reference herein.

BACKGROUND OF THE INVENTION

Mesalamine or its prodrugs/derivatives thereof are the first line therapy for the treatment of ulcerative colitis, an inflammatory bowel disease-characterized by chronic relapsing inflammation in the colon and rectum. The mechanism of action of mesalamine is unknown but appears to be topical rather than systemic. Mucosal production of arachidonic acid metabolites, both through the cyclooxygenase pathways, that is, prostanoids, and through the lipoxygenase pathways, that is, leukotrienes and hydroxy eicosatetraenoic acids, is increased in patients with chronic ulcerative colitis, and it is possible that mesalamine diminishes inflammation by blocking cyclooxygenase and inhibiting prostaglandin production in the colon.

Mesalamine dosage ranges from 1.5 g/day to the maximum of 4.8 g/day depending upon it's usage in induction or people in the United States have some difficulty in swallowing, also known as dysphagia. A survey of adults on difficulties in swallowing of the tablets and capsules suggests that this problem goes well beyond the patient population with clinically recognized dysphagia and may affect as many as 40 percent of Americans. Of those who experience difficulty in swallowing of medications, less than a quarter discuss the problem with a health care professional, 8 percent admit to skipping a dose of prescribed medication, and 4 percent have discontinued therapy because the tablets and/or capsules were difficult to swallow. Individuals who find it difficult to swallow tablets and capsules frequently cite the size as the main reason for the difficulty in swallowing.

Other adverse events such as pain, gagging, choking, and aspiration are related to swallowing difficulties in the oropharyngeal phase of swallowing and increasingly occur at larger tablet and capsules. Children and adolescents, as well as the elderly, are more likely to have difficulty swallowing tablets or capsules.

From the approved products (list provided below) for oral administration, product mesalamine sold under the trademark Pentasa™ 250 and 500 mg is available as beads (pellets) in capsules with the advantage of sprinkling in apple sauce for people who face difficulty to swallow or either for paedriatic or geriatric treatments. The other high strength products are available in tablet or capsule dosage forms, where it is not recommended or available with sprinkling characteristics.

A comprehensive list of approved mesalamine sold under the trademark Pentasa™ products for treatment of ulcerative colitis/inflammatory bowel disease, their dosage forms, and their dosage strengths are herewith listed below in Table 1.

TABLE 1

| A comprehensive list of approved mesalamine products | | | | |
|---|---|---|---|---|
| Product (Drug) | Dosage Form Description | Strength | Approx. Size of Dosage form | Pediatric Indication |
| Pentasa (Mesalamine) | Pellets in Capsule Extended Release | 250 & 500 mg | 22 mm 25 mm | No 18 years or older |
| Apriso (Mesalamine) | Pellets in Capsule Extended release | 375 mg | 23 mm | No 18 years or older |
| Lialda (Mesalamine) | Tablet DR | 1.2 gm | 20 mm | No |
| *Asacol (Mesalamine) | Tablet DR | 400 mg | 14 mm | No |
| Asacol HD (Mesalamine) | Tablet DR | 800 mg | 19 mm | No 18 years or older |
| Delzicol (Mesalamine) | 4 Units of DR tablets in a capsule | 400 mg | 22 mm | Yes 5 Years and older |

*Discontinued from the market.

remission. The other known prodrugs or derivatives of mesalamine approved for the indications for the treatment of inflammatory bowel disease such as ulcerative colitis are balsalazide, olsalazine, and sulfasalazine. Dosage of balsalazide starts with minimum of 2.25 g/day for paedriatics to maximum of 6.75/day for adults. The usual dosage of olsalazine in adults is 1.0 g/day and the sulfasalazine for initial therapy is 3-4 g/day and for maintenance therapy is 2 g/day. The dosage of sulfasalazine is adjusted according to the individual response and tolerance. The dosage levels, number of units, unit size to be administered for clinical efficacy in ulcerative colitis makes the dosage administration monotonous for paedriatics, adults and elderly patients. As per the size, shape, and other physical attributes of generic tablets and capsules guidance by FDA, over 16 million Although not all the patient factors can be addressed through pharmaceutical design and manufacture, the physical characteristics of a product can be addressed to improve the patient compliance. These physical characteristics influence the ability of certain patients to swallow the product, particularly in vulnerable populations like pediatrics, elders and others who have dysphagia. The product that can be effectively developed and manufactured to minimize swallowing difficulties, will encourage and improve patient compliance with medication regimens of larger dose and dosage forms.

Existing technologies used in preparing delayed and extended release beads of mesalamine or its prodrugs or derivatives thereof firstly involve preparation of a) granulated mesalamine, for instance, U.S. Pat. No. 8,865,688B2 discloses compositions and methods for the treatment of bowel diseases with granulated mesalamine or b) mesalamine layered sugar spheres/non pareil seeds (EP3131535A2) or c) pellets by hot melt extrusion (WO1993007859A1). They are further coated with polymer of enteric and/or delayed release characteristic.

U.S. Pat. No. 6,004,581 discloses an oral modified release composition comprising individually coated granules of mesalamine, each granule comprising: a core comprising 5-aminosalicylic acid (5-ASA) (or a salt or an ester thereof) and a spheronization aid, in particular microcrystalline cellulose, and a coating comprising a semi-permeable polymer, in particular, ethylcellulose. The granulated mesalamine preparation involves wet granulation and/or dry granulation. These processes are established to be involving multiple steps, more energy and time consuming. Also, the drug layering on sugar spheres or any inert non-pareil seeds involves the use of organic solvents, and necessitates multiple steps, thereby making the whole process more energy and time consuming. Further, the extrusion and spheronization involves multiple steps, multiple control parameters, more energy (particularly heat) and is time consuming.

R. Vijaya Muthumanikandar et al., on Design And Evaluation Of Mesalamine Tablet For colon Specific Drug Delivery, evaluated the mesalamine with other excipients for direct compression and granulation and concluded that the mesalamine is poor flow characteristic, and it needs to be granulated.

The free flow and compressibility characteristics of blends of dry ingredients are very critical to the manufacture of tablets, especially minitablets having a uniform size and weight and a degree of hardness within a narrow range.

The present disclosure discloses the composition and process where the mesalamine is directly compressible, whereas it is not granulated by wet or dry granulation process, not wetted using solvents, not melted by heating with low melting excipients, not milled for sizing, not processed by extrusion and spheronization techniques and not used sugar/non-pareil seeds. The directly compressible mesalamine or its prodrugs/derivatives composition is compressed as tablets such that the largest dimension of the tablet is not more than 2.8 mm (i.e. Minitablets).

The above information is presented as background data only to help the reader to understand the present disclosure. The Applicants have made no determination and make no assertion as to whether any of the above might be applicable as prior art with regard to the present application.

OBJECT OF THE INVENTION

The principal object of the present disclosure is to get beads in form of minitablets through non-granulated form of mesalamine and pharmaceutical acceptable excipients mixture.

Another object of the present disclosure is to get non-granulated mesalamine composition for direct compression process through specific excipients composition.

Another object of the present disclosure is to provide simple and convenient process for preparation of non-granulated mesalamine composition which is capable of being compressed into tablets without first granulating the same.

Another object of the present disclosure is to get minitablets of size not larger than 2.8 mm by compressing the non-granulated mesalamine composition.

Another object of the present disclosure is to coat the minitablets of mesalamine or its prodrugs/derivatives beads prepared using non-granulated mesalamine composition with excipients or polymeric composition of extended and/or enteric release characteristics and encapsulate as multi-unit in capsule or sachet.

Another object of the present disclosure is to administer encapsulated coated minitablets containing non-granulated mesalamine either as whole capsule or by sprinkling/dispersing/suspending the minitablets by opening the capsule or sachets in soft food/water.

Another object of the present disclosure is to administer encapsulated coated minitablets containing non granulated mesalamine equivalent to 1 g to 4 g of mesalamine in a day.

SUMMARY OF THE INVENTION

In an aspect of the present disclosure, there is provided a composition comprising: (a) mesalamine or its prodrug or derivatives thereof; and (b) at least one pharmaceutically acceptable excipient, wherein said composition is directly compressed into a minitablet; and wherein the largest dimension of said minitablet is in a range of 1.00 mm to 2.8 mm.

In an aspect of the present disclosure, there is provided a process for preparing the composition, wherein said process comprises:

a. firstly dry mixing the mesalamine with talc or other controlled release agent;

b. secondly dry mixing the first mesalamine mix obtained in step (a) with filler of d90 about 100μ to 500μ;

c. finally mixing mesalamine mix obtained in step (b) with other excipients or flow aids;

d. compressing said processed mixture obtained in step (c) to obtain a minitablet; and e. coating said minitablet obtained in step (d) with an extended and enteric polymer(s) or only enteric coating polymer(s) to obtain a coated minitablet.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

DETAILED DESCRIPTION OF INVENTION

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

The term "mesalamine" used throughout the specification refers to not only mesalamine per se, but also its pharmaceutically acceptable salts, pharmaceutically acceptable solvates, pharmaceutically acceptable hydrates, pharmaceutically acceptable enantiomers, pharmaceutically acceptable derivatives, pharmaceutically acceptable polymorphs and pharmaceutically acceptable prodrugs thereof. The amount of mesalamine used in the present disclosure is in the range from about 250 mg to about 4 g in a single or divided dose.

The term "direct compression" is used herein to refer to the process by which minitablets are compressed directly from powder blends of the active ingredients, and suitable pharmaceutical excipients, which will flow uniformly into a die cavity to form a minitablets in unform range. The advantages offered by direct compression carrier compositions in the manufacture of tablets is presented by H. A. Lieberman and L. Lachman in Pharmaceutical Dosage Forms, Vol. 1, pages 147-173, Marcel Dekker, Inc., New York (1980).

A "delayed release" composition may be designed to delay the release of the drug for a specified period. Delayed release compositions of the present disclosure include those that exhibit a delayed release, e.g., compositions that only begin releasing the drug after a fixed period of time or after reaching a specific pH. More particularly, the term "enteric coating" as used herein indicates that the coating is one that is selected for its ability to deliver active ingredients to the post-stomach gastrointestinal (GI) tract.

As used herein, the term "excipient" means any component admixed with or co-incorporated with the active agent. Excipients are safe for their intended use at the levels employed in the formulation and are compatible with the active agent. It is within the purview of the present disclosure to determine the type of excipient to be utilized in combination with the active agent as well as to determine how much excipient is to be added and the objective that the skilled artisan wishes to achieve by adding the same.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally equivalent products, compositions, and methods are clearly within the scope of the disclosure, as described herein.

The embodiments herein and the various features and advantageous details thereof are explained more fully with reference to the non-limiting embodiments detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

In an embodiment of the present disclosure, there is provided composition comprising: (a) mesalamine or its prodrug or derivatives thereof; and (b) at least one pharmaceutically acceptable excipient, wherein said composition is directly compressed into a minitablet; and wherein the largest dimension of said minitablet is in a range of 1.00 mm to 2.8 mm.

In an embodiment of the present disclosure, there is provided a composition as described herein, wherein said mesalamine or its prodrug or derivatives thereof has a weight percentage in a range of 62%-78% w/w with respect to the composition, and wherein said at least one pharmaceutically acceptable excipient has a weight percentage in a range of 22%-38% w/w with respect to the composition.

In an embodiment of the present disclosure, there is provided a composition as described herein, wherein the particle size distribution (d90) of said mesalamine or its prodrug or derivatives thereof is in a range of 100µ to 900µ.

In an embodiment of the present disclosure, there is provided a non-granulated mesalamine composition as described herein, wherein the particle size distribution (d90) of at least one excipient is in a range of 100µ to 500µ.

In an embodiment of the present disclosure, there is provided a composition as described herein, wherein said at least one pharmaceutically acceptable excipient is one or more selected from a group consisting of fillers, lubricants, anti-adherents, lubricants, glidants, binders, controlled or sustained release agents.

In an embodiment of the present disclosure, there is provided a composition as described herein, wherein said minitablet is coated with extended release and/or enteric coating polymers.

In an embodiment of the present disclosure, there is provided a composition as described herein, wherein said minitablet is encapsulated in hard gelatin or HPMC capsule or sachets or multiple dose containers.

In an embodiment of the present disclosure, there is provided a composition as described herein, wherein said composition is prepared by a process comprising:

a. a. firstly dry mixing the mesalamine with talc or other controlled release agent;

b. b. secondly dry mixing the first mesalamine mix obtained in step (a) with filler of d90 about 100μ to 500μ;

c. c. finally mixing mesalamine mix obtained in step (b) with other excipients or flow aids;

d. d. compressing said processed mixture obtained in step (c) to obtain a minitablet; and e. e. coating said minitablet obtained in step (d) with an extended and enteric polymer(s) or only enteric coating polymer(s) to obtain a coated minitablet.

In an embodiment of the present disclosure, there is provided a process to prepare said composition, wherein said composition is prepared by following order of addition of excipients: firstly with one of the flow aid or controlled release agent, then with filler and/or other excipients and finally with flow aids.

In an embodiment of the present disclosure, there is provided a quantitative composition as described herein, wherein a. Filler is at 10-34% weight by weight of total non-granulated mesalamine composition;

b. Optionally controlled or sustained release agent is at 4-34% weight by weight of total non-granulated mesalamine composition;

c. Optionally disintegrant is at 0.5-10% weight by weight of total non-granulated mesalamine composition;

d. At least one flow aid (Lubricant, Glidant and Antiadherent) is at 2-7% weight by weight of total non-granulated mesalamine composition.

In an embodiment of the present disclosure, there is provided a composition as described herein, wherein the process for preparing said composition comprises: (a) mixing mesalamine or its prodrug or derivatives thereof and at least one pharmaceutically acceptable excipient to obtain a mixture; (b) compressing said processed mixture of step (a) to obtain a minitablet; and (c) coating said minitablet with an extended and enteric polymer(s) or only enteric coating polymer(s) to obtain a coated minitablet.

In an embodiment of the present disclosure, there is provided a composition as described herein, wherein the process for preparing said composition comprises: (a) mixing mesalamine or its prodrug or derivatives thereof and at least one pharmaceutically acceptable flow aid or controlled release agent to obtain a mixture; (b) further processing said mixture of step (a) with fillers and/or other excipients; (c) processing (b) with other flow aids (d) compressing said processed mixture of step (c) to obtain a minitablet; and (e) coating said minitablet with an extended and enteric polymer(s) or only enteric coating polymer(s) to obtain a coated minitablet.

In an embodiment of the present disclosure, there is provided a composition as described herein, wherein the process for preparing said composition comprises: (a) mixing mesalamine or its prodrug or derivatives thereof and at least one pharmaceutically acceptable flow aid or controlled release agent in a twin shell blender or similar low shear apparatus to obtain a mixture; (b) further processing said mixture of step (a) with fillers and/or other excipients in a twin shell blender or similar low shear apparatus; (c) processing (b) with other flow aids again in a twin shell blender or similar low shear apparatus (d) compressing said processed mixture of step (c) to obtain a minitablet in multi-tip punches in a single or double rotary compression machine; and (e) coating said minitablet with an extended and enteric polymer(s) or only enteric coating polymer(s) in a perforated coating pan to obtain a coated minitablet.

In an embodiment of the present disclosure, there is provided a composition as described herein, wherein the process for preparing said composition comprises: (a) mixing mesalamine or its prodrug or derivatives thereof and at least one pharmaceutically acceptable flow aid or controlled release agent in a twin shell blender or similar low shear apparatus for 100 revolutions to 200 revolutions to obtain a mixture; (b) further processing said mixture of step (a) with fillers and/or other excipients in a twin shell blender or similar low shear apparatus for 50 revolutions to 100 revolutions; (c) processing (b) with other flow aids again in a twin shell blender or similar low shear apparatus for 30-100 revolutions (d) compressing said processed mixture of step (c) to obtain a minitablet in multi-tip punches in a single or double rotary compression machine at turret speed of 5 to 15 rpm; and (e) coating said minitablet with an extended and enteric polymer(s) or only enteric coating polymer(s) in a perforated coating pan to obtain a coated minitablet.

In an embodiment of the present disclosure, the coated minitablets of step (e) are encapsulated with suitable fill weight to obtain a capsule or sachet of desired label claim.

In an embodiment of the present disclosure, there is provided a composition as described herein, wherein the coated minitablets may be encapsulated into capsule of "0EL" or "00" size for whole administration or by opening and dispersing in water or by opening and spreading in apple sauce or any soft foods of pH below 6.

In an embodiment of the present disclosure, there is provided a composition as described herein, wherein the coated minitablets encapasulated in sachets are to be administered by dispersing in water or by spreading/suspending in apple sauce or any soft foods of pH below 6.

In an embodiment of the present disclosure, the coated minitablets can be packed in multiple unit dose containers by weight, wherein beads of respective unit dose prescribed are to be dispensed either qualitatively (in a tablespoon or teaspoon) or quantitatively (in a volumetric device) for oral administration.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may apply.

C—The mesalamine is first mixed with retarding agents like Eudragit S100 for 10 mins at 15 RPM in twin shell blender, then the filler is added and mixed in twin shell

TABLE 2

Weight of non-granulated mesalamine composition for direct compression in mg

| Ingredients | T1 | T2 | T3 | T4 | T5 | T6 | T7 | T8 | T9 |
|---|---|---|---|---|---|---|---|---|---|
| Mesalamine | 375 | 375 | 375 | 375 | 375 | 375 | 375 | 375 | 375 |
| Microcrystalline cellulose | | 27 | 27 | 27 | 27 | 60 | 200 | 150 | 150 |
| Dicalcium Phosphate | 27 | | 20 | 20 | 20 | 30 | | | |
| Polyvinyl pyrrolidone | 20 | | | | | | | | |
| Magnesium Stearate | 8 | 8 | 8 | 8 | 8 | 10 | 10 | 10 | 10 |
| Talc | 5 | 5 | 5 | 5 | 5 | 5 | 5 | 5 | 5 |
| Silicon Dioxide | 10 | 10 | 10 | 10 | 10 | 20 | 10 | 10 | 10 |
| Total | 445 | 425 | 445 | 445 | 445 | 500 | 600 | 550 | 550 |
| Process Method | A | A | A | A | A | A | B | B | B |
| Multi tip Punch Diameter | 2 mm | 2 mm | 1.25 mm | 2.00 mm | 2.00 mm | 2.00 mm | 2.00 mm | 2.00 mm | 1.25 mm |
| Physical Observations | Very Poor flow | Poor Flow | Poor Flow | Poor Flow | Poor Flow | Good flow, capping and few soft tablets | Good flow, no capping or soft tablets | Good flow, no capping or soft tablets | Good flow, no capping or soft tablets |

Weight of non-granulated mesalamine composition for Direct compression in mg

| Ingredients | T10 | T11 | T12 | T13 | T14 | T15 | T16 | T17 | T18 |
|---|---|---|---|---|---|---|---|---|---|
| Mesalamine | 375 | 375 | 375 | 375 | 375 | 375 | 375 | 375 | 375 |
| Microcrystalline cellulose | 130 | 120 | 75 | 75 | 75 | 75 | 135 | 135 | 75 |
| Glyceryl Dibehenate | 20 | 30 | | | | | | | |
| Eudragit S100 | | | 20 | 20 | | | | | |
| Partially pregelatinized Starch | | | | | | 10 | 10 | 10 | |
| Magnesium Stearate | 10 | 10 | 10 | 5 | 10 | 10 | 10 | 10 | 10 |
| Talc | 5 | 5 | | | 10 | 10 | 10 | 10 | 10 |
| Silicon Dioxide | 10 | 10 | 10 | 5 | 10 | 10 | 10 | 10 | 10 |
| Total | 550 | 550 | 490 | 490 | 480 | 490 | 550 | 550 | 480 |
| Process Method | B | B | C | C | B | B | A | B | B |
| Multi tip Punch Diameter | 2 mm | 1.25 mm | 2 mm | 2.00 mm | 2.00 mm | 2.00 mm | 2.00 mm | 2.00 mm | 1.25 mm |
| Physical Observations | Good flow, no capping or soft tablets | Good flow, no capping or soft tablets | Good flow, no capping or soft tablets | Poor flow, Sticking issues, Weight variation, Punch tip Bending | Good flow, no capping or soft tablets | Good flow, no capping or soft tablets | Good flow, no capping and few soft tablets | Good flow, no capping or soft tablets | Good flow, no capping or soft tablets |

Process

A—The mesalamine is first mixed with filler in twin shell blender for 10 mins at 15 RPM, further the binder or disintegrants are added (if applicable) and mixed for 5 mins at 15 RPM, then finally the flow aids are added and mixed for 5 mins at 15 RPM.

B—The mesalamine is first mixed with talc for 10 mins at 15 RPM in twin shell blender, then the filler is added and mixed in twin shell blender for 5 mins at 15 RPM, finally the disintegrants (if applicable) and flow aids are added and mixed for 5 mins at 15 RPM.

blender for 5 mins at 15 RPM, finally the flow aids are added and mixed for 5 mins at 15 RPM.

After compressing into minitablets, the minitablets are coated with enteric or extended release polymers or with both (like Eudragit L30D 55 or Eudragit L100 or mixture of Eudragit L & S polymers) for desired release profile.

Results

Contacting and mixing the poorly flow mesalamine with micronized talc (i.e. process B) or retarding agents like Eudragit S100 (process C) coats the mesalamine and gives non adherence nature and free flowing properties, further addition of directly compressible grade fillers and flow aids at percentage gives free flowing nature to achieve the uniform flow for die filling and compression of minitablets.

Contacting and mixing the poorly flow mesalamine retarding agents like Eudragit S100 (process C) coats the mesalamine and gives non adherence nature and subsequent addition of directly compressible grade fillers and then flow aids at NLT 2% imparting a free flowing powder for uniform compression. Whereas the reduction in final flow aids at 2% or less resulting in poor flow from hopper and in die's, also gives sticking issues, weight variation (due to carry forward of sticking, double compression) and tip bending.

Contacting and mixing the poorly flow mesalamine initially with fillers or microcrystalline cellulose and then the other excipients doesn't result in proper flow from hopper or into dies.

Advantages of the Present Disclosure

The present disclosure provides a directly compressed minitablet composition of mesalamine or its prodrug or derivatives thereof, where its largest dimension is in the range of 1.00 mm to 2.8 mm of any common pharmaceutical tablet shapes for oral administration. The tablets are further coated with enteric or extended release coating polymers and encapsulated into a capsule or sachets or multiple unit dose containers for oral administration. Existing technologies used in preparing delayed and extended release dosage forms of larger dose mesalamine or its prodrugs or derivatives thereof firstly involve preparation of a) granulated mesalamine or b) mesalamine layered sugar spheres/non pareil seeds or c) pellets by hot melt extrusion or d) encapsulating the a) or b) or c) as such after the desired choice of coating to target site of release or e) compressing the a) or b) or c) into minitablets and encapsulated after the desired choice of coating to target site of release. They are further coated with polymer of enteric and/or delayed release characteristic. The granulated mesalamine preparation involves wet granulation and/or dry granulation which involves multiple unit processing like mixing, binder preparation, granulation/compaction, drying, milling. These processes are established to be involving multiple steps, more energy and time consuming. Also, the drug layering on sugar spheres or any inert non-pareil seeds involves the use of organic solvents, and necessitates multiple steps, thereby making the whole process more energy and time consuming. Further, the extrusion and spheronization involves multiple steps, multiple control parameters, more energy (particularly heat) and is time consuming. To overcome the above drawbacks the present disclosure discloses non-granulated, directly compressed, pharmaceutical compositions of mesalamine or its prodrugs/derivatives as minitablets such that the largest dimension of the minitablet is less than 2.8 mm. The composition of the present disclosure is devoid of non-pareil seeds, organic solvents, and the processes adopted to prepare the composition are free of milling, extrusion and spheronization technique, and granulation processes.

We claim:
1. A minitablet composition comprising:
a. mesalamine or its prodrug or derivatives thereof; and
b. pharmaceutically acceptable excipients,
wherein:
said pharmaceutically acceptable excipients comprises: (a) 75-200 mg microcrystalline cellulose having 90% of particles having a diameter of from about 100 μm to 500 μm as measured by laser diffraction technique; (b) 5-10 mg of talc or 20-30 mg of glyceryl dibehenate or 5-10 mg of pregelatinized starch; (c) 5-15 mg of silicon dioxide; and (d) 5-15 mg of magnesium stearate;
said minitablet composition is a non-granulated composition and directly compressed into a minitablet; and largest dimension of said minitablet is in the range of from 1.00 mm to 2.8 mm; and
said mesalamine or its prodrug or derivatives thereof are present in an amount of 62%-78% w/w with respect to the composition and having d90 of from 100 μm to 900 μm as measured by laser diffraction technique.

2. The minitablet composition as claimed in claim 1, wherein said pharmaceutically acceptable excipient is present in an amount of 22%-38% w/w with respect to the composition.

3. The minitablet composition as claimed in claim 1, wherein said minitablet is coated with extended release and/or enteric coating polymers.

4. The minitablet composition as claimed in claim 1, wherein said minitablet is encapsulated in a hard gelatin capsule, or hydroxypropyl methylcellulose capsule, or sachets.

5. The minitablet composition as claimed in claim 1, wherein said composition is prepared by:
a. firstly dry mixing mesalamine or its prodrug, or derivatives thereof with talc or glyceryl dibehenate for 10 mins at 15 rpm with twin shell blender to obtain first mesalamine mixture;
b. secondly dry mixing the first mesalamine mixture obtained in step (a) with microcrystalline cellulose having 90% of particles having a diameter of from about 100 μm to 500 μm, as measured by laser diffraction technique, for 5 minutes at 15 rpm to obtain mesalamine mixture;
c. finally mixing the mesalamine mixture obtained in step (b) with partially pregelatinized starch, silicon dioxide, and magnesium stearate for 5 minutes at 15 rpm to obtain processed mixture;
d. compressing said processed mixture obtained in step (c) to obtain a minitablet; and
e. coating said minitablet obtained in step (d) with an extended and enteric polymer(s) or only enteric coating polymer(s) to obtain a coated minitablet.

* * * * *